United States Patent [19]

Schneider et al.

[11] 4,451,568
[45] May 29, 1984

[54] COMPOSITION FOR BINDING BIOACTIVE SUBSTANCES

[75] Inventors: Michel Schneider, Troinex; Pierre Chevreux, Ferney-Voltaire; Christian Guillot, Saint Nicolas le Vieux, all of Switzerland

[73] Assignee: Battelle Memorial Institute, Carouge, Switzerland

[21] Appl. No.: 285,182

[22] PCT Filed: Nov. 13, 1980

[86] PCT No.: PCT/CH80/00138

§ 371 Date: Jul. 13, 1981

§ 102(e) Date: Jul. 13, 1981

[87] PCT Pub. No.: WO81/01412

PCT Pub. Date: May 28, 1981

[51] Int. Cl.$^3$ ............... C12N 11/06; C12N 11/08; E08F 2/46
[52] U.S. Cl. ............... 435/181; 204/159.22; 204/159.23; 428/420; 435/174; 435/180
[58] Field of Search ............ 435/174, 176, 177, 180, 435/181, 182; 204/159.22, 159.23; 428/420

[56] References Cited

U.S. PATENT DOCUMENTS

| | | | |
|---|---|---|---|
| 3,759,807 | 9/1973 | Osborn et al. | 204/159.23 |
| 3,826,678 | 7/1974 | Hoffman et al. | 428/420 |
| 3,844,892 | 10/1974 | Matthews | 435/181 |
| 3,859,169 | 1/1975 | O'Driscoll et al. | 435/182 |
| 4,070,246 | 1/1978 | Kennedy et al. | 435/181 X |
| 4,070,348 | 1/1978 | Kraemer et al. | 435/180 X |
| 4,071,409 | 1/1978 | Messing et al. | 435/176 |
| 4,132,596 | 1/1979 | Meiller et al. | 435/180 |
| 4,141,851 | 2/1979 | Levy et al. | 435/180 X |
| 4,178,221 | 12/1979 | Boutin et al. | 204/159.22 X |
| 4,269,941 | 5/1981 | Ichimura et al. | 435/180 X |
| 4,297,185 | 10/1981 | Chevreux et al. | 404/159.22 X |

OTHER PUBLICATIONS

Mayairi et al., Photoimmobilization of Enzyme Chem. Abstr., vol. 89: 19234p, 1978, (p. 258).
Iida et al., Immobilized Enzyme or Microbe. Chem. Abstr., vol. 88: 117046c, 1978, (p. 207).
Iida et al., Maintenance of Immobilized Enzyme or Microbe. Chem. Abstr., vol. 88: 117048e, (1978), (p. 207).
Goudd et al., Formation of a Stabilized Enzyme by Inclusion in a Water-Soluble Hydrophilic Polymer, vol. 80: 243279, 1974, (p. 181).
Kaetsu et al., Enzyme Immobilization by Polymers, vol. 84: 3309c, 1976, (p. 301).

Primary Examiner—David M. Nafe
Attorney, Agent, or Firm—Kenneth R. Warburton; Benjamin Mieliulis; Philip M. Dunson

[57] ABSTRACT

An acrylic-acid- based photopolymerizable composition is prepared which is capable of binding bioactive substances after being photopolymerized. The composition may be applied as a coating on a carrier substrate, photopolymerized and a bioactive substance fixed thereto. The composition adheres well to any usual carrier substrates, and its degree of hydrophilicity and permeability can be adapted to needs. The composition contains acrylic acid, a photoinitiator which is an aromatic ketone compound, a photopolymerization activator and adhesion promotor which is an amino-alcohol, acrylate or methacrylate, and a copolymerizable olefinic monomer which contains a reactive functional group capable of binding bioactive substances. The olefinic monomer is preferably N-hydroxysuccinimide acrylate, N-hydroxysuccinninimde amidocaproate, epoxypropyl acrylate or 2-isocyanato-ethyl acrylate.

19 Claims, No Drawings

COMPOSITION FOR BINDING BIOACTIVE SUBSTANCES

TECHNICAL FIELD

The present invention concerns the field of biologically active synthetic products and, more especially, that of substrates the surface of which possesses a biological activity, e.g. enzymatic activity or other.

Considerable work has been carried out in the past years for developing materials, in plain or divided form, the surface of which enables to link, permanently or temporarily, biologically active molecules. By the term of "biologically active molecules" there is understood, in general, molecules that participate in the chemical processes on which living beings are dependent. Among such substances, there can be recited enzymes, enzyme inhibitors, molds, hormones, antigens, antibodies, biological inhibitors, heparin, lectins, etc. These molecules generally have one or more reactive sites specific of some or another reaction or distinctive process and, by extension, there will be used in the present specification the term of biological or biofunctional molecules for substances of synthetic origin which behave similarly and are capable of functioning as biocatalysts, biosorbents, etc.

Thus, such carrier materials comprising a biofunctional substance can act, toward a substrate, as would the corresponding biofunctional substance in the free state; however, at the end of the reaction, such materials can generally be isolated from the reaction medium by usual means without any particular difficulty, which possibility does not necessarily hold for biologically active substances in the free state.

One particularly well known example of such biologically active materials is that of resins coated or impregnated with an enzyme; such materials, once activated, are put in the presence of a substrate to be biochemically modified in such a way as to have a reaction between the latter and the active layer of the material to take place. Once the reaction is at its end, the active material can be separated by usual means from the reaction medium and it can generally be reused directly or, if necessary, its activity can be restored by an appropriate regenerating treatment. Thus, when such biofunctional substances are tied up in an inert carrier and when, in such conditions, they are active toward a substrate to be transformed, they are often named as "biocatalysts". Similarly, a "biosorbent" is a substrate to which there are bonded biofunctional molecules capable of catching a substance that one desires to separate from a mixture.

REVIEW OF THE PRIOR-ART

Amidst the recent and more significant publications in the field, the following documents can be cited as examples:

1. Pellicular Immobilized Enzymes by C. Horvath, Biochem. & Biophys. Acta 338 (1974), 164–167. This reference stresses the advantages resulting from using thin films of an enzyme containing substrate as compared with using a column filled with particles of such substrate in comminuted form, e.g. a column loaded with resin particles containing enzymes immobilized within the mass of said resin. Indeed, the action of such substrate on a solution put in contact therewith is essentially of superficial nature and the use of thin films of active material coated on a rigid carrier is profitable because of obvious reagent savings and because of better mechanical stability. This reference indicates, particularly, that materials involving thin layers coated on a rigid supporting carrier, a glass bead for instance, activated by enzymes can be classified into three main categories, namely:

(a) The enzyme is trapped in a gel like matrix, the enzyme being bonded to the gel before or after depositing the latter on the carrier.

(b) The carrier consists of a micro-porous layer made, for instance, from a mineral or organic absorbent medium (silica, alumina, carbon, porous nylon, etc) and the enzyme is attached to this substrate by coupling or by cross-linking on the surface thereof.

(c) The organic or mineral film-like carrier is macroporous (pore size of about 100–200 nm); it can be impregnated with a polymer enzyme conjugate solution, after which the solvent is evaporated to leave said conjugate deposit on the carrier. In such case, the system hence comprises, as a whole, three distinct phases: (i) an inert carrier (e.g. glass beads) coated with (ii) a first carrier substrate (e.g. a macroporous inert polymer), the surface of the pores of the latter being itself covered by (iii) a layer of an enzyme containing polymer.

Besides, the same reference discloses, with regard to the materials belonging to the above category (b), a method for coating glass beads with a solution of a polymer with a high proportion of —COOH groups (a maleic anhydride-methyl-vinyl ether) and, after drying, for activating this polymer film by contacting with aqueous solutions of enzymes such as trypsin, chymotrypsin, protease, ribonuclease, papain, etc.

2. French Pat. Nos. 2.028.702 and 2.035.774 disclose the binding of biologically active molecules, such as enzymes, antigens, allergens, hormones, etc. to organic or mineral supporting carriers such as cellulose, starch, alginates, collagen, polysilanes, polyacrylic resins, glass, metals, etc., by using bridging agents such as diazo compounds, epoxides, carbodiimides, sulfonyl chloride and dialdehydes, glutaraldehyde for instance. Glutaraldehyde also acts as a cross-linking agent for such biologically activated molecules.

A similar method is also described in the following article: Preparation and Properties of Urease Chemically Attached to Nylon Tubes by P. V. SUNDARAM et al, FEBS letters 10 (5), 325 (1970) as well as in published German patent application DOS No. 2.636.206.

3. East-German Pat. No. 106.856 (CA 82, 82332 q) discloses the manufacture of a polyacrolein gel in which urease has been incorporated by mixing.

4. U.S. Pat. No. 3,844,892 (CA 82, 82328 t) describes the trapping of glucose oxidase by the reaction with an epoxide containing co-polymer obtained by the co-polymerization of acrylo-nitriles and epoxy-acrylic esters. The bonding of the enzyme thus takes place there by the reaction of the latter with the oxirane groups of the copolymer.

5. Japanese patent application Kokai No. 75/10.585 (CA 83, 159962a) discloses the polymerization of a mixture of asparaginase, acrylamide, a stabilizer and a polymerization initiator, the whole being coated as a thin layer on the wall of a glass tubing.

6. Japanese patent application Kokai No. 75/70.584 (CA 83, 159963b) also discloses a polymeric film in which an enzyme is embedded. This polymer consists of a mixture of the enzyme (aminoacylase) with acrylamide, N,N'-methylene-bis-acrylamide, β-aminopropionitrile and $K_2S_2O_7$ which was coated and polymerized on a fritted hydrophilic carrier.

7. Japanese patent application Kokai No. 76/63.985 (CA 85, 107494w) describes the formation of a copolymer similar to that mentioned under item (5) above and its use for decomposing aspartic acid in a blood solution which is circulated in contact with this active polymer.

8. Japanese patent application Kokai No. 77/145.592 (CA 88, 117050z) describes the preparation of a nitrocellulose film containing an enzyme, this film being obtained by adding the enzyme to a solution of the polymer in an organic solvent, then by coating the mixture on a cross-linked nylon supporting carrier and by drying the coating thus obtained.

Some other methods have photopolymerization processes; Thus:

9. German patent application DOS No. 2.305.320 (CA 80, 24327q) discloses: the incorporation of an enzyme (urease) into poly(2-hydroxyethyl)-methacrylate; then the coating of the resulting mixture on a polyethylene supporting carrier; the hardening of this coating under irradiation (UV); and the protecting of the coating of this film by a new layer of poly(2-hydroxyethyl)-methacrylate to provide an enzymatically active and storage stable film.

10. A. TANAKA and al, J. Ferment Technol. 1977, 55 (1), 71–75 mention the trapping of enzymes or microbial cells into photocrosslinkable resins such as polyethylene glycol dimethacrylate.

11. Japanese patent application Kokai No. 77/151.788 (CA 88, 117046c) describes the trapping of enzymes in a photohardenable resin dispersion. According to this reference, a resin obtained from polyethylene glycol, 2-hydroxyethyl methacrylate and xylene diisocyanate is mixed with a diatomaceous earth powder and a photoinitiator, after which there is added an aqueous solution of enzyme (invertase) and the mixture is irradiated with a UV light for providing an enzymatically active mass.

12. Japanese patent application Kokai No. 77/143.279 discloses suspending a biologically active protein into a liquid photosensitive resin containing a water-soluble photosensitizer, the whole being thereafter emulsified in an aqueous phase and irradiated so as to achieve the trapping ("immobilization") of said protein by photopolymerization of the resin particles that contain the latter.

13. Japanese patent application Kokai No. 77/143.282 (CA 88, 117048e) describes a method according to which a mixture of an enzyme and a photopolymerizable resin is irradiated by means of UV light, this mixture having be used beforehand for impregnating a porous supporting carrier, for instance a textile filaments fabric, the whole giving then a flexible strap covered with an enzymatically active film.

14. In Japanese patent application Kokai No. 75/78.641 (CA 84,3309c), there is described the mixing of an enzyme in aqueous solution (glucose isomerase) and a photopolymerizable acrylic monomer, then the conversion by UV irradiation of this mixture into a polymer powder containing "immobilized" therein, the enzyme under an active form.

15. In Japanese patent application Kokai No. 78/34.984 (CA 89,19234p), there is described a method according to which there are mixed an enzyme (β-glucosidase), a photocrosslinking monomer for binding the enzyme (4,4'-diazidostilbene-2,2'-disulfonate) and an aqueous solution of gelatin; then a film of this mixture (50 μm) is deposited on a glass plate after which irradiation is carried out so as to provide an enzymatically active film.

The following references concern the preparation of materials in comminuted form, the particles of which are covered with a biologically active preparation, the active molecules being generally bound to the substrate carrier by bridging.

16. U.S. Pat. No. 4,070,246 (CA 88, 117052b, 1978) describes a process according to which there is suspended a metallic powder in an aqueous mixture of p-aminobenzoic acid and formaldehyde after which the powder coated with the polymer that results from the condensation of these compounds if filtered out, it is subjected to diazotization and the diazotized substrate is coupled with an enzyme so as to bind the latter to the polymer.

17. In U.S. Pat. No. 4,071,409 (CA 88, 117053 c, 1978), there is described the treatment of a carrier substrate, such as powdered silica or rutile, with a diisocyanate, this reagent functioning, in this case, as a bridging agent for fixing, on the substrate, an enzyme such as papain.

18. U.S. Pat. No. 4,072,566 (CA 88, 117054 d) discloses a method according to which p-phenylenediamine is adsorbed on porous glass particles, the aromatic amine is diazotized and the diazotized product is coupled with papain.

19. U.S. Pat. No. 4,077,089 (CA 86, 116834 a) describes the use of 1-N(2-nitro-4-azidophenyl)-6-N'(4,6-dichloro-triazinyl)-diaminohexane for bridging enzymes and antibodies on organic water insoluble supporting carriers, the azido group being transformed into a nitrene group under UV irradiation and attaching itself to the carrier while the triazinyl group attaches to the enzyme protein molecule.

20. Japanese patent application Kokai No. 76/31.689 (CA 85, 47837y) describes the treatment of hydroxylated carrier substrates (e.g. silica gel) with aminosilanes and polymers containing dinitrobenzene-pyridinium groups so as to enable these substrates to stably bind enzymes.

21. French Pat. No. 2.235.133 (CA 83, 74687 q) describes the fixing of enzymes (aminotransferase) on collagen films or fibers after first activating the carrier with HCl, then providing bridging links by treating with hydrazine in the presence of nitrous acid.

22. German patent application DOS No. 2.323.422 describes the preparation of copolymers of 2-hydroxyethyl methacrylate and ethylene glycol dimethacrylate containing, covalently bound thereto, biologically active molecules such as enzyme inhibitors, enzymes, antigens, antibodies, etc., respectively. Comminuted resins constituted by such polymers provide activated filling charges able to catch, when in contact with solutions, the conjugated moieties of the substances bonded to said polymer, i.e. enzymes, enzyme inhibitors, antibodies, antigens, etc., respectively.

Besides the chemical bridging achieved by the method mentioned hereinabove, there can also be mentioned the binding of enzymes on supporting carriers by grafting methods which involve the use of more or less energetic radiations. Thus, 23. H. BARKER et al, Proc. Int. Congr. Catal., 6th (1976), Publ. Chem. Soc. Letchworth, Engl., (CA 87, 196426g) describe the grafting under irradiation of monomers such as p-nitrostyrene on supporting carriers such as polyolefines and PVC, the $NO_2$ group being thereafter converted to an isothiocyanate group which is an enzyme fixing group (trypsine). As possible irradiation sources, the reference recites γ-rays, electron beams and UV.

24. In the article of A. S. HOFFMAN et al, Trans. Am. Soc. Artif. Intern. Organs 1972, 18, 10–18, there is indicated that grafting has been achieved under γ-irradiation on supporting carriers of silicone rubber. The grafted substances were hydrogels of photopolymers containing 2-hydroxyethyl methacrylate, and N-vinyl-pyrrolidone, the grafting being achieved directly or with the intermediate use of ε-aminocaproic acid. These hydrogels then enabled the chemical bonding of biological molecules such as albumin, heparin and streptokinase, the whole providing biologically active substrates.

25. Similarly, A. S. HOFFMAN et al in Am. Chem. Soc. Div. Org. Coat. Plast. Chem. Pap. 1974, 34 (1), 568–73 review the known methods for fixing, by means of irradiation techniques, hydrophilic polymers on inert supporting carriers, biologically active molecules being then, afterwards, chemically bondable to the free —OH, —COOH, etc. groups of these hydrophilic polymers.

26. Such methods are also described by A. S. HOFFMAN in the following references: Polym. Prepr. Ames. Chem. Soc., Div. Polym. Chem. 1972, 13 (2), 740–6 and 723–8; U.S. Pat. No. 3,826,678.

An improvement in the preparation of polymers capable of binding biologically active molecules consists, in contradistinction with the principle of immobilization by trapping said molecules in the mass of the polymer or by grafting them on a given carrier substrate, in preparing a copolymer from a basic monomer for achieving the formation of the back-bone itself of the copolymer and another monomer linked to a biologically active molecule or bearing a reactive group capable of binding, later on, a biologically active molecule, this bonding being achieved, either directly, or by means of an additional chain (spacer arm) enabling to maintain the active molecule at a given distance from the substrate; this distance is generally adapted so that the displacements of the portions of molecules which come into play during the biological reaction are not hindered by being too close to that substrate.

27. French Pat. No. 2.212.340 thus discloses a method according to which there is polymerized or co-polymerized an enzyme carrying monomer in the presence of a crosslinking agent and an initiator, the bound enzyme being, for instance, urease, amyloglucosidase, glucose oxidase, fumarase, aspartase and penicillin aspartase.

28. In German patent application DOS No. 2.426.988, there is described the fixation of enzymes to carrier substrates with covalent bond by copolymerizing an activated polysaccharide and a monomer, the latter having a group capable of bonding to an enzyme. As a modification, there is also described the bonding of an enzyme to a copolymer by crosslinking the latter with a crosslinking agent to which said enzyme has been attached beforehand.

It is useful at this stage to give some particulars on the applications of biologically active substrates, especially when they are in the form of thin layers deposited on organic or mineral supporting carriers. One of the major applications of such substrates is represented by the automatic analysis of some biological fluids, a typical example of which is provided by the determination of glucose in blood and in serum. After appropriate dilution and possibly dialysis, the sample to be analyzed is circulated in a circuit comprising, as the reactive element, a tube or a set of tubes the internal wall of which is coated with a coating enzymatically active toward the solution to be analyzed. After leaving said element, the products from the reaction of the solution and the coating are analyzed by usual methods, e.g. by continuous spectrophotometry. Thus, the active element of such analytical device must keep its enzymatic properties unmodified with time and, further, it must possess sufficient specificity and stability for warranting that the results are reproducible for a prolonged work period. Besides, the specific activity of the active coating should be high for avoiding to have an element with too cumbersome dimensions. The state of the art in this field can be illustrated by the following references:

29. Open Tubular Heterogeneous Enzyme Reactors by C. HORVATH and B. A. SOLOMON, Biotechnology & Bioengineering 14, 885–914 (1972).

30. L. P. LEON et al, Clin. Chem. 22/7, 1017–1023 (1976); 23/9, 1556–1562 (1977).

In view of the references mentioned, it can be concluded that, for the time being, the technology of thin layer enzymatically active coatings on rigid supporting carriers includes the following processes:

A. Gels containing, in immobilized form, the biofunctional molecules, these gels being deposited, as coatings, on a supporting carrier.

B. Porous substrates deposited, as thin layers, on a carrier and containing the enzymes in an absorbed state or covalently linked thereto.

C. Carrier, the surface of which (generally smooth or rough) has been activated, either chemically or by irradiation, so as to become apt to bind the enzymes, either directly or by means of a bridging agent.

D. Coating of a polymeric resin containing the enzyme, either trapped in its mass, or attached by covalent bonds.

In all cases, the main problems related to providing layers with satisfactory operating efficiency are the followings:

(a) Effective contact surface between the solution to be treated and the active substrate must be as large as possible, meaning that the penetration of said solution into the active coating should be good; the gels or the porous substrates must have a high porosity; the polymer resin matrixes should be swellable in the solutions; the polymers used should be hydrophilic.

(b) The specificity of the nature of the receiving and bonding sites for the bioactive molecules should be selected depending on the desired objectives: providing a substrate with a permanent biological activity or, otherwise, temporary catching, for extrations, and subsequent release of an active substance (enzyme purification or affinity chromotography).

(c) The possibility of using all the available active mass, or nearly so, some biofunctional substances being very expensive, whereby it should be possible to produce active coatings of which only the portions that are being accessible to the solution to be treated should contain the active molecules.

(d) Faultless adhesion of the active substrate on its carrier.

Yet, at the present time, none of the known techniques permits reconciling simultaneously to a high degree all these requirements. Thus, it is difficult to firmly adhere gels and porous substrates to inert carriers and, besides, it is difficult to control the permeability and the porosity thereof so as to ensure the free and efficient circulation of the solution to be treated between the active sites.

Moreover, the direct treatment of carriers by chemical routes or by irradiation often lacks efficacy (surface bonding density insufficient); furthermore, highly energetic irradiations (γrays) may have a destructive effect on said carriers.

On the other side, the present methods lack versatility which means that each particular case must be approached with a specific technique often very different from that required by an apparently similar case which only differ therefrom by an apparently insignificant feature. Thus, for instance, it is not possible with the known techniques to provide an enzymatically active composition which is suitable for porous glass as well as for smooth polyethylene, i.e. that can be directly applied equally well to both such carriers, without having to subject one or the other of these carriers to some specific preliminary treatment.

DISCLOSURE OF THE INVENTION

The present invention remedies these drawbacks and embodies a technique which is simultaneously simple and more versatile as it practically applies to all contemplated carrier substrates and is suitable, with minor and easily foreseable modifications, for obtaining thin layer biofunctional substrates of a virtually limitless variety.

For achieving this, the invention encompasses a photoadhesive composition (I). This composition practically adheres to any usual supporting carrier, mineral or organic: glass, ceramics, metals, woods, synthetic resins, etc. i.e. any carrier which can reasonably be contemplated for such an application, this being without having to subject the surface of these carriers to any particular treatment. The composition of the invention has an acrylic acid base; it comprises, (i) a photoinitiator and, furthermore, (ii) a photopolymerization activator and adhesion promoter (for enabling a fast photo-adhesion and photo-setting and ensuring a sufficient adhesion of the photopolymerized coating on the carrier). The composition also comprises (iii) at least one monomer comprising a grouping suitable to catch, by bonding directly or by means of an intermediate arm previously connected to this grouping, an instantly or potentially biologically active substance.

By "potentially biologically active" (as compared to "directly or instantly active"), it is meant a molecule having normally biofunctional properties but that can be inactivated under certain conditions, e.g. by coupling with an inhibitor or by blocking the one or several reactive sites thereof.

When the photo-adhesive composition of the invention has been applied to a supporting carrier, the whole is subjected to photo-irradiation, e.g. by means of UV, which causes the copolymerization of acrylic acid, the monomer (iii) and other copolymerizable substances optionally present in the composition. One thus obtains a hydrophilic photopolymerized resin coating (II) adhering strongly to mineral or organic, synthetic or natural supporting carriers, superficially permeable to water and swellable in the presence of the latter, this resin containing, in the copolymerized state, at least one type of segment apt to link, by a direct bond or by means of an intermediate arm previously or subsequently attached to that segment, one or several macromolecular active substances (or potentially active), this being with adequate stability and without having the instant or potential activity of these substances be significantly altered or modified. Naturally, such a photopolymerized coating (II) is also a part of the invention as well as the supporting carrier provided with such a coating.

When the photopolymerized coating is on its carrier, biologically active substances can be affixed thereto, either by direct contact therewith, or by the attachment beforehand of an intermediate arm (pi) the free end of which comprises a function apt to bind the biofunctional substance, either permanently (covalence), or temporarily (complexation). In this last case, the intermediate arm is considered a specific ligand of the molecule to be caught. The photopolymerized coating carrying biofunctional molecules (or potentially biofunctional molecules) (III) is also part of the invention as well as the carrier with such a coating.

BEST MODES OF CARRYING OUT THE INVENTION

When the biofunctional molecules are bound to the substrate of the invention, there is thus obtained a bioactive product (or potentially bioactive) which can be put to work in the various applications for which it has been designed. For instance, when the coating carries an enzyme, the carrier substrate is put in contact with a solution of materials to be treated by means of this enzyme so as to carry out the reaction, continuously or discontinuously. Then, the reaction medium is separated from the active carrier substrate which is recovered and reused as many times as it is desired. According to another example, if a biofunctional molecule must be removed from a mixture with other substances, there is operated as above by means of substrate (II), then the substrate (III) loaded with said molecule is separated and, by means of an appropriate treatment, one causes the rupture of the complex and the liberation of the captured molecule. It is also understood that the present invention covers the use of coatings (II) and (III) as active agents in the biochemical conversion reactions specific to the biofunctional substances bonded to said coatings or carrier substrates. Such agents can sometimes be defined as "biocatalysts".

As it has been seen above, the composition (I) of the invention is based on acrylic acid. This monomer is particularly well convenient because it imparts to the copolymers made therewith favorable hydrophilic properties and, further, it easily and rapidly photopolymerizes with suitable photoinitiators. In contrast, methacrylic acid is not recommended for the composition (I), because it does not photopolymerize rapidly enough.

As photoinitiators (i), one can use in composition (I) aromatic ketones commonly used as photo-promoters for polymerization (see for instance U.S. Pat. No. 3,759,807). There can be mentioned, benzophenone, acetophenone and the corresponding halogenated compounds. One can also use anthraquinone compounds such as 2-ethyl-anthraquinone, anthraquinone-2-carboxylic acid, as well as other photoinitiators such as benzoin, 2,5-diethylaminophenyl-1-oxy-3,4-diazole and naphthylene sulfochloride.

As a polymerization activator and adhesion promoter (ii), one preferentially uses an amino-alcohol acrylate or methacrylate such as dimethylaminoethyl methacrylate (DMAEMA). However, other amino-alcohol methacrylates can also be used such as N-diethylaminoethanol and N-ethyl-N-tert.butyl-aminoethanol. The use of such activators in adhesive compositions is known (see French Pat. No. 2.881.968 and Swiss Application CH 9815/78.

In addition to acrylic acid as the basic monomer of the present copolymer, the composition can also contain other olefinic monomers such as acrylamide, acrylic and methacrylic esters, polyfunctional acrylates and acrylic prepolymers. Monofunctional acrylic esters and acrylamide can be added for imparting improved homogeneity and more adequate viscosity to the adhesive composition and, in addition, to control the hydrophilicity of the copolymers after hardening. The quantities of such additives must therefore be varied by skilled operators according to the needs as a function of the properties to be given to the contemplated copolymer. Among the esters which can be advantageously used, there can be recited the acrylates and methacrylates of lower alkyl radicals (methyl, ethyl, propyl, butyl, isobutyl, tert.butyl, etc.) of the dodecyl radical, of the ethylhexyl radical, of the methoxyethyl radical, etc. Polyfunctional radicals can be used for giving more rigidity to the present copolymer according to the needs. As such, one can recite trimethylol-propane triacrylate (TMPTA), pentaerythritol triacrylate (PETRA) and the corresponding tetraacrylate (PETEA).

The acrylic or vinyl prepolymers can be added in small quantities to the composition of the invention when one desires to impart thereto more flexibility and resilience. As such prepolymers, one can recite the compounds known under commercial names such as UVITHANE (Thiokol Corporation) and EBECRYL (Union Chimique Belge). Similar prepolymers are described in British Pat. No. 1.430.422 and German patent application DOS No. 25.42.314.

Monomers (iii) having a reactive function capable of binding biofunctional molecules, either directly or by means of an intermediate arm, are extremely diverse and can be selected from case to case according to the needs. Generally, they must have an olefinic double bond (for instance acrylic or vinyl) and, when for instance a large peptide molecule must be linked directly (enzyme, enzyme inhibitor, antigen, antibody, etc.), they will comprise a functional group capable of reacting with, for instance, an amino group of said molecule to be caught. Compounds containing such functional groups (acylating agents, protective groups, compounds bearing "leaving groups") are abundantly described in the literature devoted to the synthesis of polypeptides. Most olefinic monomers with such functional groups can be suitable for the present invention. As examples, the following compounds can be mentioned: N-hydroxysuccinimide acrylate, N-hydroxysuccinimide acrylamido-caproate, epoxypropyl acrylate, 2-isocyanato-ethyl acrylate. In general, other similar monomers in which the double bond and the functional groups are separated from each other by a hydrocarbon chain of a length exceeding that of the above mentioned monomers can be advantageous in the case when it is desired to provide more freedom to the biofunctional molecule, i.e. to maintain it, for reasons for steric hindrance, at a greater distance from the carrier substrate. In general such a hydrocarbon chain can have from 5 to 15 carbon atoms.

When it is wanted to fix bioactive molecules on the carrier substrate by means of monomer (iii) and through the intermediacy of an intermediate bridge (pi), said monomer (iii) comprises, in addition to the double bond, a reactive group capable of easily forming, with an appropriate compound, said intermediate bridge. As such reactive groups, there can be recited the groups —OH, esters, —COOH, —NH$_2$, etc. Consequently, as the monomers suitable for the introduction of such groups, there can be recited ethylene glycol monoacrylate, glycol monoacetate acrylate, 2-aminoethanol acrylate, maleic anhydride and other similar monomers.

As Examples of intermediate arms (pi), one can use carbodiimides (reaction on —COOH groups with the formation of acylureas which are reactive with protein molecules); hydrazine (reacting with esters and forming, with HNO$_2$, azide groups which react with enzymes); diisocyanates (which can bind on one side on —OH groups (urethanes) or —NH$_2$ (ureas) and, on the other side on the bifunctional molecules to be caught. Generally, said intermediate arms comprise at their free end a functional group capable of reacting with the biofunctional molecule and to bind the latter to the carrier substrate, the definition of such group being the same as that given hereinabove.

In a more detailed manner, one can still add the following examples of terminal ligands capable of providing moieties for fixing biofunctional molecules on the coating of the invention: aminobenzamidine which is specific for trypsin; 4-phenylbutylamine specific for chymotrypsin; dyestuffs such as CIBACHRON BLUE F3G-A and PROCION RED HE-3B specific for dehydrogenases; sugars such as maltose that is specific for certain lectins as well as D-galactosamine specific for galactosidases; iminodiacetic acid (IDA) which, under the form of its zinc salt specifically complexes some plasma proteins ($\alpha$-globulins, $\gamma_2$-macroglobulines); lysine as well as butyl p-aminobenzoate which are specific for plasminogen. Other Examples are found in the book "Methods in Enzymology", Vol. 14.

The proportions of the various ingredients which the present composition can contain are extremely diverse and can be easily adapted, according to the needs, by a skilled technician. However, in general, the proportions of acrylic acid should not be too low so that the copolymer has sufficient hydrophilicity and can be comprised between about 10 and 70% by weight of the composition and, preferably, between 20 and 50% by weight. The concentration of the photoinitiator (i) is 0.5 to 10%, preferably around 1 to 5% for ensuring that the photopolymerization is efficient and the proportion of the activator and promoter (ii) is from 0.5 to 15%, the preferred range being 4 to 8% by weight. The quantity of monomer (iii) depends essentially from the specific activity to be imparted to the copolymer once the latter is coated on its supporting carrier. Such an activity begins already to be significant when the composition contains only relatively small quantities of the monomer (iii) but, in practice, one often seeks to obtain specific activities (per unit area) as large as possible. In such a case, one may incorporate to the composition up to 30% or even 50% of monomer (iii), the upper limt being set up by the physical properties of the coating resulting from the copolymerization. Indeed, too large quantities of monomer (iii) can lead to some coating defects: lack of hydrophilicity, lack of adhesiveness, brittleness, etc.

When the present composition contains, in addition, an acrylic ester, the latter can replace in part the acrylic acid and its concentration can be from 0 to about 60%. The other acrylate described above (polyfunctionals or the prepolymers) can optionally be added in small quantities not exceeding, in general, 5 to 10%. It should however be noted that the concentrations given above are not critical and, in some special cases, they can exceed the given limits.

Regarding the preparation of the present adhesive composition, this can be easily achieved by mixing the various selected ingredients, it being well understood that they must be mutually compatible. The mixing can be effected by usual means, namely a mixing mill. Once obtained, the mixture is allowed to stand for a few hours for equilibration purposes after which it can be stored in the dark or it can be used directly for the preparation of adhesive coatings. For preparing such coatings, the composition is deposited on a supporting carrier using common techniques: brush, spraying, doctor's knife, etc. As already said, practically all carrier substrates are convenient: plates, beads, tubings with smooth or rough surfaces, glass, metals, plastic resins, polyolefines, nylon, PVC, Spandex resins, etc. In practice, it is preferred for instance to treat beads of glass or of synthetic resins since such beads can be used, afterwards, as biocatalysts in various laboratory and industrial devices: purification columns, containers for treating biological liquids, etc. It is also possible to coat very thin polyethylene films which, once folded or spirally wound, provide a very large contact surface in a tiny volume; it is also possible to impregnate a polyurethane foam (transparent to UV) so as to obtain a porous structure the internal surface of which, when coated with a film of the present composition, is strongly enlarged. According to another embodiment of application, the composition is sprayed on the internal surface of a tube and the coating thus obtained is subsequently used as an analytical element in an automatic measurement apparatus for determining some constituents of biological fluids. The quantity of composition that is used per unit area of the supporting carrier can be very small. Indeed, it has been noted that when the surface of the activated coating from the present composition is contacted with a fluid to be treated, only a thickness corresponding to a few molecular layers is involved (10-20 nm approximately). Thus, the working thickness of the coatings from the present composition can be made very thin (of the order of 0.1 to 5 $g/m^2$) which is a significant economical advantage.

Once the present composition is spread over all or part of the carrier substrate, its hardening by photoirradiation is undertaken. When the carrier is transparent, one can irradiate on the front side or, preferably, on the back side, this providing better adhesion.

As irradiation sources, there can be used any electromagnetic source the emission spectrum of which comprises, at least mainly, the spectral range above 0.3 micron, for instance a mercury vapor lamp. There are preferably used one or several mercury vapor lamps of a power between 20 W and 10 KW.

For instance, there can be used a mercury vapor lamp with a 2 KW nominal power such as a HTQ7 PHILIPS lamp or a 5 KW high pressure mercury vapor lamp delivering 80 W/cm of mark HANOVIA. Argon or krypten lamps are also suitable.

The irradiation period required for polymerizing the adhesive corresponds to the minimal irradiation dose of appropriate wave length received by the adhesive layer. This period thus essentially depends on the source power, its spectral range and on the distance from the source to the coating.

However, when implementing the invention, a satisfactory polymerization and adhesion on most possible carrier substrates can be obtained with very short irradiation periods (comprised for instance between 0.5 sec and several min depending on the source power and its emission spectrum characteristics). Further, this adhesion is little, or not, altered when the substrate carrier is put, after activation, into contact with aqueous solutions, namely the solutions with which it is reacted.

Once the photopolymerized coating (II) is obtained, its activation is undertaken. For this, either a direct activation by putting the carrier substrate with the biofunctional molecule or molecules to be caught must be considered, or an activation by means of the above described intermediate arm.

In the first case, one proceeds very simply, generally by immersing the supporting carrier with its reactive substrate into a solution of the substance to bind and leaving it there, under agitation, for the time required for reaching a sufficient extent of binding. In practice, the carrier substrate is dipped into an aqueous solution, for instance of an enzyme and is left in contact with this solution from a few minutes to several hours, after which the activated substrate is washed until the washing waters do not further contain any free enzyme.

In the second case, one starts by effecting the fixation of the intermediate arm according to the methods already mentioned hereinbefore or according to the methods exhaustively described in the references recited in the introduction to this specification. Then, one proceeds to the binding of the biofunctional molecules as described above. In the examples given hereinafter, precise details are given on the manners to achieve several embodiments of the invention.

In summary, the present invention has, over the techniques of the prior-art, the following advantages:

Very simple and rapid implementing procedure. The specificity of the attaching sites is very high and the degree of activation and the nature of the bound molecules can be very well controlled. Extremely versatile method, although using a commonly based adhesive composition, by simply varying the nature of the monomer to be copolymerized. Simple and well defined structure for the polymer and also for the biological catalyst obtained therefrom. The degree of hydrophilicity and of permeability of the polymer can be adapted to the needs. Practically, any carrier material is suitable.

According to a typical example of application of an activated substrate (III) according to the invention, the internal walls of glass tubes are coated by spraying with a layer of about $1\mu$ of a composition (I) containing N-hydroxysuccinimide acrylate as the monomer (iii) and this is irradiated for 10 sec with a 2 KW UV source distant 15-20 cm from the tube. Then, by dipping the first half of the tubes into an aqueous solution of glucose oxidase, a portion of the coating is activated, the second portion thereof being activated by immersing the second half of the tubes into a peroxidase solution. After activation, the tube is installed, as the active element, in an apparatus for the automatic determination of glucose in biological fluids, the solution going across the tube in the direction glucose oxidase→peroxidase.

During the analysis, the glucose contained in the solution flowing through the first half of the tube is decomposed in the presence of the glucose oxidase with liberation of $H_2O_2$, the existence of which is depicted by its oxidizing actions on an indicator (p-tolidine, blue color), this action being catalyzed by the peroxidase of the second half of the activated tube.

A related method enables one to determine the quantity of antigen in a biological fluid because of the high degree of reproducibility and reliability and the activity specificity of the coatings according to the invention. The operation proceeds as follows: A coating of determined specific activity is prepared by spraying in the inside of a given tube a known quantity of composition and, after irradiation, the coating thus obtained is activated to a reproducible and determined level by contacting with a solution of antibody. Then a known proportion of labelled antigen* (radioactive) is added to the solution to be analyzed and the latter is contacted with the activated substrate for the time required to saturate the active sites thereof. The level of radioactivity of the residual solution is then measured which enables to calculate, by subtraction, the quantity of tagged antigen caught and, as a consequence and as a function of the theoretical quantity having to be absorbed by the coating, the proportion of unmarked antigen originally present in the sample.

The following examples illustrate the invention in detail.

Laboratory and Industrial Applications

EXAMPLE 1

Preparation of an adhesive composition (I)

In a mixer mill there were intimately mixed the following ingredients: acrylic acid 58,4%, 2-(dimethylamino)-ethyl methacrylate (DMAEMA) 13%, N-hydroxysuccinimide 26%, benzophenone 2,6%.

The mixture was allowed to stand for several hours, then a thin layer of the composition was spread on a surfaced glass plate by means of a manual hand coater; and then, for protecting the coat from the outside atmosphere, it was covered with an untreated polyester sheet which was applied without pressing with a rubber roller.

Irradiation and preparation of the coating (II)

The glass plate thus prepared was subjected to 2 min of irradiation with a PHILIPS lamp (Type HTQ7, 28 W/cm) placed at 15 cm from the substrate. Then the polyester sheet was removed which came off easily. The coating thus obtained was colorless, strong and not brittle; its thickness was approximately 8 μm.

Activation and preparation of the activated substrate (III)

The plate was dipped into an aqueous 100 mg/l trypsin solution (SIGMA) at pH 7.5 (0.5 M phosphate buffer) and it was left immersed therein for 4 hours at room temperature. Then the plate was withdrawn from the solution and it was noted that the coating had markedly swollen but it adhered still perfectly to its carrier. The plate was washed carefully with 0.5 M phosphate buffer and its specific activity was measured against an aqueous $10^{-3}$ M solution of benzoyl-arginine p-nitroanilide. Under the enzymatic action of the activated plate, this compound did liberate p-nitroanilide which was determined spectrophotometrically at 410 nm. The enzymatic hydrolysis rate of this substrate in solution was 22 μmole/min at room temperature.

It was derived therefrom that the specific activity of the active coating was 50 μg of trypsin/cm$^2$.

EXAMPLE 2

One proceeded as described in example 1 and a photoadhesive composition (I) was prepared from:

Acrylic acid 32.5%; butyl acrylate 32.5% DMAEMA 6.5%; N-hydroxysuccinimide acrylamidocaproate 26% benzophenone 2.5%.

This composition (stored at about 40° C. for preventing it from crystallizing by cooling) was applied to the inside of a 6,6-polyamide tubing (CELLPACK A.G., CH-5610, WOHLEN+AG) of the following dimensions: useful length 5 cm; diameter 0.15 cm; useful internal surface 2.35 cm$^2$. For doing this, the tube was filled with the adhesive composition; and then it was emptied by letting the liquid out by gravity; then the excess of liquid was expelled by means of a draft of compressed air which was blown through the tube for 3–5 sec. Then a slow current of nitrogen was circulated through the tube while subjecting the latter for 6 min to the action of a 2 KW UV light placed at 15 cm and slowly axially rotating the tube during the irradiation. Then, as in the previous Example, the tube thus prepared (phase II) was immersed into an aqueous solution of trypsin and, after 4 hrs at room temperature, it was noted that the specific activity of the coating (phase III) was of 36 μg of trypsin/cm$^2$.

A series of twelve similar tubes was prepared in the same way and there was noted that the specific activity of each of these tubes was about the same. These tubes were bundled together and placed into a glass tube of about 1.2 cm diameter so as to constitute an active element the total activity of which was about 1000 mg of trypsin.

EXAMPLE 3

One proceeded as described in the previous examples and an adhesive composition was prepared that contained: acrylic acid 35%, isopropyl acrylate 30%; DMAEMA 6.5%; 2-hydroxyethyl acrylate 26%; benzophenone 2.5%.

One hundred grams of this composition were diluted with 100 ml of methyl-ethyl-ketone and this mixture was sprayed as a fine mist inside of polyamide tubes (of the same type as of Example 2), so as to deposit on the surface thereof, a film of about 1 μm thick. Then the tubes were rapidly dried under nitrogen, after which the coating was irradiated as described in Example 2. Then the tubes were immersed 15 min at room temperature in a 60% solution of butylene diisocyanate in CHCl$_3$, after which the tubes were rinsed with chloroform so as to eliminate the excess of diisocyanate and they were rapidly dried under N$_2$.

For rendering the coating biofunctional, one proceeded as follows: two tubes were placed in series and there was circulated therethrough for two hours at room temperature, at the rate of 1 ml/min 10 ml, a 1.5% heparin solution (SIGMA, 170 units USP/mg). Then the tubes were washed with a 0.9% solution of NaCl and there was circulated therein at 37° C. a solution constituted of a mixture of 0.3 ml of plasma, 0.3 ml of a thrombine solution (~2.4 NIH units (National Institute of Health, USA)) and 0.3 ml of physiological solution. After circulating for 1 min, the coagulation time of this solution was measured by the standard technique, the value found being 44 sec. As a comparison, a control sample of the above solution was circulated in a set of two identical tubes placed in series, but the coating of which had not been activated with heparin, and there was then measured a coagulation time of 18 sec. Obviously, heparin had been well bonded to the coating according to the invention and the tube thus prepared had a significant anticoagulating efficiency.

EXAMPLE 4

There was used the same adhesive composition as that described in Example 2 and using a coating device involving a doctor's blade, there was deposited a film of about 2–3μ on a bioriented polypropylene sheet of 12 μm thickness.

This sheet was moved under the protection of a nitrogen current blown at the surface in the form of a laminar flow, before a UV light of 28 W/cm, so that each portion of this sheet was irradiated 3 sec at a distance of 8 cm. Then the sheet was cut into $5 \times 10$ cm strips which were wound up lengthwise in spirals so as to obtain cylinders which were introduced into polyamide tubes similar to that described in Example 2. Once the spirally wound up cylinder was in the tube it underwent relaxation so as to provide between the windings free spaces of about 2–5μ thickness.

The tubes were then immersed into an aqueous trypsin solution and, after proceeding as described in Example 2, there was obtained an activated substrate the specific activity which was about 30 μg of trypsin/cm$^2$. The tubes were then brought together as bundles of 12 as described in Example 2 which provided active elements of about 6 cm$^3$ volume, the total active surface of which was about 600 cm$^2$ and the activity of about 18 mg of trypsin. This element was tested by circulating therethrough at the rate of 5 ml/min at $10^{-3}$ M solution of benzoylarginine ethyl ester which caused the practically quantitative liberation of the benzoylarginine (determined by titration according to usual means).

EXAMPLE 5

There was prepared an adhesive composition identical with that of Example 2, but with replacement of the active monomer thereof by N-acryloyl-N'-t.butoxycarbonylhydrazine of formula CH$_2$=CH—CO—NH—NH—COO-t.Bu. This composition was deposited on a propylene sheet as described in the previous Example and, after irradiation, there were prepared tubes provided with a spirally wound sheet of this polymer still as in the previous Example.

For making these tubes biofunctional, one proceeded as follows: There was circulated for 2 hours therein a 2 M HCl solution at 30° C.; after which they were rinsed with the same solution cooled to 0° C. There was then introduced and allowed to react for 5 min at 0° C. a 1 M HCl and 1 M NaNO$_2$ solution; then the tubes were rapidly rinsed at 0° C. with a borate buffer, pH 7.5. Then there were circulated in the tubes for 2 hrs a 0.1 M solution of p-aminobenzamidine in a borate buffer, pH 8.5 at the rate of 1 ml/min; then the tubes were rinsed with the borate buffer alone. On an other side, there was prepared in a 0.02 M Ca$^{++}$ ions solution an aqueous extract of oxen pancreas as described at Example 11 (see hereinafter) and the latter was activated by adding a small portion of trypsin and agitating slowly for 3 hrs at pH 8.5. A precipitate had then formed which was separated by centrifugation. Fifty ml of the clear supernatent liquid were taken and circulated for 1 hr in a set of 10 tubes prepared as described above, placed in series, at the rate of 2 ml/min. The tubes were washed with 0.1 M tris.HCl buffer, pH 1.7 at 0° C., then diluted HCl, pH 1.7, was circulated at 0° C. which caused the trypsin retained by the coating of the tubes to get released. Finally, the extract was dialyzed with a regenerated cellulose standard membrane and after freeze drying, the concentrate provided 14 mg of a product with a high trypsin content and corresponding to 64% of the total quantity of trypsin of the centrifugated starting liquid, as measured with BAPNA (cf. Example 1).

EXAMPLE 6

In a plate of expanded polyethylene of 2 cm thickness (foam with opened structure) there was cut with a punch (cork punch) a cylinder of 4 mm diameter. This foam "stopper" was impregnated with the adhesive composition of Example 2; then it was introduced into a quartz tube of 4 mm diameter and it was pressed and triturated with a rod so as to expell as much as possible of the adhesive liquid. Then the tube was connected to a compressed nitrogen source and, while circulating this gas through the tube at a very slow rate, the latter was irradiated for 6 min while under rotation as in Example 2.

After hardening of the adhesive, the substrate was activated by circulating through the tube a 100 mg/ml trypsin solution. After saturating the coating with trypsin, a standard BAPNA solution (see Example 1) was circulated through the tube. By the determination of the p-nitroaniline liberated by hydrolysis it was estimated that the activity of the trypsin bonded to the foam was about 240 μg.

EXAMPLE 7

In an alumina cylindrical container, there were placed 100 g of glass beads of about 1 mm diameter and about 0.6 g of the adhesive composition of Example 2. The container was rotated for 2 hrs on a horizontal roller mixer, after which about 0.3–0.4 g of these beads were introduced into a tube of 5 mm diameter and of about 2 cm long. Then, this tube was irradiated for 6 min at room temperature as described in the previous Examples while circulating therein a slow nitrogen flow. After polymerization, the thickness of the coating (phase II) was measured by refractometry and found to be about 3 μm. Then, the beads were biofunctionally activated (phase III) as described in Example 2.

EXAMPLE 8

A polyamide tube was selected of the same type of those described in Example 2, length 5 cm; diameter 0.15 cm and it was internally coated with a copolymer layer by means of the adhesive composition of said same Example 2.

There was circulated for 3 hrs in this tube an aqueous solution containing the following ingredients: borate buffer 0.5 M, pH 8.5; NaCl 0.5 M; glucose oxidase 100 mg/ml (MERCK 16 U/mg).

The tube was placed in a bath at 25° C. (temperature stabilized by thermostat) and, by means of a peristaltic pump, there were progressively and successively circulated samples, 1 ml each, of glucose solutions (in a phosphate buffer 0.1 M and pH 7.0), the concentration of which was increased stepwise from 0.5 g/l to 2.5 g/l; after the passage of each glucose sample, there were circulated intermediate separating portions of 1 ml of phosphate buffer (0.1 M, pH 7.0). The flow rate in the tube was 3 ml/min. After leaving the activated tube, the samples were collected, one after the other, in small cuvettes containing each 0.1 ml of aqueous o-dianisidine solution (0.7 mg/ml) and 0.1 ml of peroxidase solution (1 mg/ml) in phosphate buffer 0.1 M, pH 7.0. After mixing, the solutions of the cuvettes underwent color development and the intensity of this color was measured spectrophotometrically at 436 nm. The results of the measurements (optical densities) are tabulated in Table I below:

TABLE I

Analysis of glucose by the reaction $O_2$ + glucose (glucose oxidase) → $H_2O_2$ + o-dianisidine (peroxidase) → dyestuff

| Sample | Solution of glucose g/l | Optical density Lg $I/I_0$ (436 nm) |
|---|---|---|
| 1 | 0.5 | 0.12 |
| 2 | 1 | 0.242 |
| 3 | 1.5 | 0.363 |
| 4 | 2 | 0.47 |
| 5 | 2.5 | 0.58 |

Thus, one notices that an almost linear relation exists between the glucose concentration and the optical density of the colored solution. Thus, it is possible to use the activated coating according to the invention as the analytical element for determining glucose in aqueous solutions of unknown concentration.

The enzymatically active coating is particularly stable and its activity maintains itself practically unchanged for a long time.

Still further, there were circulated in the same tube described above successive samples of 1 ml glucose solutions separated by portions of 1 ml of phosphate buffer at 0.1 M, pH 7.0, the concentration of said samples being alternately 0.2 g/l and 2 g/l. One then proceeded as described above to spectrophotometrically measure the obtained colorations and the following results were found.

TABLE II

| Sample | Solution of glucose g/l | Optical density (436 nm) |
|---|---|---|
| 6 | 0.2 | 0.045 |
| 7 | 2.0 | 0.465 |
| 8 | 0.2 | 0.05 |
| 9 | 2.0 | 0.47 |
| 10 | 0.2 | 0.05 |

The above results indicate that no carry-over phenomenon will disturb the measurements when a strong glucose concentration is replaced by a concentration 10 times less and vice-versa. The method thus accepts a high range of concentrations with a high degree of reliability. Further, the enzymatically active coating is perfectly stable and its activity maintains itself practically unchanged for a long period.

EXAMPLE 9

There were placed in a 20 ml pipet 21 g of 1 mm glass beads covered with a photopolymerized coating (phase II) such as described in Example 7. Then an aqueous solution of 100 mg/ml of chymotrypsin (SIGMA) in a phosphate buffer 0.5 M, pH 7.5 was circulated through the pipette for 3 hrs. The pipette was then carefully rinsed with 0.5 M phosphate buffer and the specific activity of the coating then enzymatically activated was measured with the p-nitroanilide of N-glutaryl-L-phenyl-alanine (GLUPHEPA). This method, described for instance by B. F. ERLANGER et al in Arch. Biochim. et Biophys. 115, 206 (1966) is based on the cleavage of the above nitroanilide with liberation of p-nitroanilide which is measured spectrophotometrically at 410 nm. There was thus established that the activity of the column was 60 μg of chymotrypsin per cm² of the bead coating, the total surface available of these beads being about 300 cm².

By means of the above column, one proceeded to the continuous hydrolysis of a 1% casein solution in 0.1 M phosphate buffer, pH 7.6. One liter of this solution was passed through the column at the rate of 2 ml/min and it was noted, after analysis of the hydrolyzate by the usual means, that the conversion yield exceeded 90%. The analysis was performed according to the method of KUNITZ, Methods in Enzymology, Vol. II, P.33. For this, there is added trichloracetic acid to an aliquot of the solution to be measured and, after separation by centrifugation of the precipitate formed, the absorbence of the remaining liquid is measured at 280 nm.

After letting the column at rest for 48 hrs in the presence of 0.1 M phosphate buffer, another 1 liter solution at 1% of casein was again passed in the tube at the same rate as previously and, after analyzing the hydrolyzate, it was noted that the enzymatic activity of the activated tube had remained unchanged.

EXAMPLE 10

A polyethylene film, coated with a layer of adhesive composition, was prepared as described in Example 4.

Before subjecting the film thus coated to photopolymerization, it was sprayed with an alumina powder of about 5 μm mesh size at the rate of 0.5–1 g/m². Then the film was irradiated as already described and it was cut into strips which were spirally wound and slipped into tubes as described in Example 4. The alumina particles stuck to the surface of the adhesive prevented the successive windings of the strip from adhering to each other and provided enough space between each winding to enable a liquid to easily circulate through the tube.

An aqueous 0.5 M phosphate buffer, pH 7.5, containing 100 mg/ml of trypsin (SIGMA type IX) was circulated for 3 hrs in one of these tubes. Then the tube was rinsed with the phosphate buffer and the enzymatic activity of the operative coating was determined with benzoyl-arginine p-nitroanilide (BAPNA) as follows: five ml of a $10^3$ M solution of BAPNA was circulated in the tube for 5 min (flow rate 3 ml/min). Then the solution thus treated was analyzed spectrophotometrically at 410 nm (absorption peak of the p-nitroaniline). Afterwards, the magnitude of the trypsin equivalent attached to the substrate was determined by comparison with a standard calibration curve, this curve representing the amount of p-nitroaniline as a function of the quantity of trypsin acting on an equivalent solution of BAPNA. In the present case, the activity of the coating was evaluated to be about 30 μg of trypsin per cm².

EXAMPLE 11

In a polyamide tube of 1.5 mm diameter and 1 m long, there was circulated a 30% solution of the adhesive composition of Example 3 in $CHCl_3$. The tube was carefully drained by gravity after which a slow nitrogen flow at 40° C. was circulated therein. After 10 min, during which period, the remnants of $CHCl_3$ were evaporated, the tube was subjected to irradiation with a UV lamp that was displaced parallelwise along the tube while rotating the latter on itself so that each portion of the tube was subjected to the radiation from the lamp for about 4 min at 15 cm distance.

The tube was thereafter filled, by aspiration, with a 25% toluene diisocyanate solution in chloroform and, after waiting 15–20 min, the tube was emptied and washed with dry chloroform. After drying the tube with a dry nitrogen flow there was circulated through the tube a 50 mg/ml solution of soja inhibitor (FLUKA) in borate buffer at pH 9. Then the tube was rinsed with distilled water. On an other side, a fresh oxen pancreas was ground and homogenized in 600 ml of distilled water, the suspension was centrifuged and the supernatant liquid was circulated in the tube activated as described above. The traces of trypsin contained in this solution were retained by the internal coating of the tube whereas the zymogenic substances of the extract (easily transformed by the trypsin) remained in solution unchanged. It was thereafter possible to treat this extract, purified from the unwanted trypsin, so as to isolate the zymogenic substances by usual means, the latter being thus obtained in a particularly high yield.

We claim:

1. An acrylic-acid-based photopolymerizable composition capable of binding bioactive substances after being photopolymerized comprising:

10 to 70 percent by weight of acrylic acid, and
   (i) 0.5 to 10 percent by weight of at least one photoinitiator which is an aromatic ketone compound;
   (ii) 0.5 to 15 percent by weight of at least one photopolymerization activator and adhesion promotor which is an amino-alcohol, acrylate, or methacrylate; and
   (iii) an effective amount up to 50 percent by weight of at least one copolymerizable olefinic monomer having a double bond, which is copolymerizable with the acrylic acid and which has a reactive functional group capable of binding bioactive substances, said monomers being selected from the group consisting of N-hydroxysuccinimide acrylate, N-hydroxysuccinimide amidocaproate, epoxypropyl acrylate and 2-isocyanato-ethyl acrylate, said effective amount being an amount to provide sufficient reactive functional groups to bind said bioactive substances.

2. The composition of claim 1 wherein the olefinic monomer in (iii) has connected thereto an intermediate arm moiety having a reactive functional group selected from the group consisting of hydrazino, hydroxyl, ester, carboxy and amino.

3. The composition of claim 1 or 2 in which said composition comprises:
   20 to 50 percent by weight of the acrylic acid, and
   (i) 1 to 5 percent by weight of the photoinitiator;
   (ii) 4 to 8 percent by weight of the photopolymerization activator and adhesion promotor;
   (iii) up to 30 percent by weight of the copolymerizable olefinic monomer.

4. The composition of claim 1 wherein the 10 to 70% by weight of acrylic acid consists of a combination of acrylic acid and an acrylic ester, said acrylic ester comprising not more than 60% of the combination by weight.

5. The composition of claim 4 wherein the combination further includes from 5 to 10% by weight of an acrylate selected from the group consisting of polyfunctional acrylates and prepolymer acrylates.

6. A photopolymerized resin of the composition of claim 1.

7. The photopolymerized resin of claim 6 in which there are bound by said reactive functional groups bioactive substances selected from the group consisting of enzymes, enzyme inhibitors, antigens, antibodies, lectins, microbes, hormones and heparin.

8. The photopolymerized resin of claim 7 in which the monomer has connected thereto an intermediate arm moiety having a reactive functional group selected from the group consisting of hydrazino, hydroxyl, ester, carboxy and amino and in which the bioactive substances are bound to the reactive functional groups included in said intermediate arm moiety, and separated by a hydrocarbon chain of from 5 to 15 carbon atoms from the double bond of said olefinic monomer.

9. A photopolymerized resin of the composition of claim 3.

10. A photopolymerized resin of the composition of claim 4.

11. A hydrophilic coating adhering to a carrier substrate, which coating is a photopolymerized resin of an acrylic-acid-based photopolymerizable composition which is capable of binding bioactive substances comprising:
    10 to 70 percent by weight of acrylic acid, and
    (i) 0.5 to 10 percent by weight of at least one photoinitiator which is an aromatic ketone compound;
    (ii) 0.5 to 15 percent by weight of at least one photopolymerization activator and adhesion promotor which is an amino-alcohol, acrylate, or methacrylate; and
    (iii) an effective amount up to 50 percent by weight of at least one copolymerizable olefinic monomer having a double bond which is copolymerizable with the acrylic acid and which has a reactive functional group capable of binding bioactive substances, said monomers being selected from the group consisting of N-hydroxysuccinimide acrylate, N-hydroxysuccinimide amidocaproate, epoxypropyl acrylate and 2-isocyanato-ethyl acrylate, said effective amount being an amount to provide sufficient reactive functional groups to bind said bioactive substances.

12. The hydrophilic coating of claim 11 wherein the olefinic monomer in (iii) has connected thereto an intermediate arm moiety having a reactive functional group selected from the group consisting of hydrazino, hydroxyl, ester, carboxy and amino.

13. The hydrophilic coating adhering to a carrier substrate of claim 11 or 12 in which said coating is the photopolymerized resin of the acrylic-acid-based photopolymerizable composition comprised of:
    20 to 50 percent by weight of the acrylic acid, and
    (i) 1 to 5 percent by weight of the photoinitiator;
    (ii) 4 to 8 percent by weight of the photopolymerization activator and adhesion promotor; and,
    (iii) up to 30 percent by weight of the copolymerizable olefinic monomer.

14. The hydrophilic coating adhering to a carrier substrate of claim 11 wherein the 10 to 70% by weight of acrylic acid consists of a combination of acrylic acid and acrylic ester, said acrylic ester comprising not more than 60% of the combination by weight.

15. The hydrophilic coating of claim 14 wherein the combination further includes from 5 to 10% by weight of an acrylate selected from the group consisting of polyfunctional acrylates and prepolymer acrylates.

16. The hydrophilic coating adhering to the carrier substrate of claim 11 in which the carrier substrate is an organic or mineral supporting carrier material and there are bound by said reactive functional group bioactive substances selected from the group consisting of enzymes, enzyme inhibitors, antigens, antibodies, lectins, microbes, hormones and heparin.

17. A process for preparing on a substrate a polymeric resin coating capable of binding bioactive substances, which process comprises the steps of:
(a) mixing an acrylic-acid-based photopolymerizable composition comprising
10 to 70 percent by weight of acrylic acid, and
(i) 0.5 to 10 percent by weight of at least one photoinitiator which is an aromatic ketone compound;
(ii) 0.5 to 15 percent by weight of at least one photopolymerization activator and adhesion promotor which is an amino-alcohol, acrylate, or methacrylate; and
(iii) an effective amount up to 50 percent by weight of at least one copolymerizable olefinic monomer having a double bond, which is copolymerizable with the acrylic acid and which has a reactive functional group capable of binding bioactive substances said monomers being selected from the group consisting of N-hydroxysuccinimide acrylate, N-hydroxysuccinimide amidocaproate, epoxypropyl acrylate and 2-isocyanato-ethyl acrylate, said effective amount being an amount to provide sufficient reactive functional groups to bind said bioactive substances;
(b) applying this mixed composition as a thin film on the substrate; and
(c) irradiating the film for a time and at a wavelength adapted to polymerize said composition.

18. The process of claim 17 which includes: in step (c) irradiating with an actinic source and a subsequent step (d) contacting the polymerized film with a biofunctional substance to bond the same thereto.

19. The process of claim 18 wherein the olefinic monomer in (iii) has connected thereto an intermediate arm moiety having a reactive functional group selected from the group consisting of hydrazino, hydroxyl, ester, carboxy and amino.

* * * * *